(12) United States Patent
Jeong et al.

(10) Patent No.: US 10,194,891 B2
(45) Date of Patent: Feb. 5, 2019

(54) MINIMALLY INVASIVE SURGICAL INSTRUMENT HAVING ARTICULATION IMMOBILISING STRUCTURE

(71) Applicant: MOVASU, INC., Seoul (KR)

(72) Inventors: Chang Wook Jeong, Seoul (KR); Hyung Tae Kim, Seoul (KR)

(*) Notice: Subject to any disclaimer, the term of this patent is extended or adjusted under 35 U.S.C. 154(b) by 916 days.

(21) Appl. No.: 14/390,287

(22) PCT Filed: Mar. 26, 2013

(86) PCT No.: PCT/KR2013/002472
§ 371 (c)(1),
(2) Date: Oct. 2, 2014

(87) PCT Pub. No.: WO2013/151262
PCT Pub. Date: Oct. 10, 2013

(65) Prior Publication Data
US 2015/0066001 A1    Mar. 5, 2015

(30) Foreign Application Priority Data

Apr. 2, 2012 (KR) .................. 10-2012-0034090

(51) Int. Cl.
*A61B 17/00* (2006.01)
*A61B 17/29* (2006.01)

(52) U.S. Cl.
CPC ........ *A61B 17/00234* (2013.01); *A61B 17/29* (2013.01); *A61B 2017/003* (2013.01);
(Continued)

(58) Field of Classification Search
CPC ............. A61B 17/00234; A61B 17/29; A61B 2017/003; A61B 2017/2927; A61B 2017/2946
(Continued)

(56) References Cited

U.S. PATENT DOCUMENTS

2005/0096694 A1* 5/2005 Lee .................. A61B 17/00234
606/205
2005/0182298 A1* 8/2005 Ikeda ................. A61B 1/00149
600/146
(Continued)

FOREIGN PATENT DOCUMENTS

JP    2008-049104 A    3/2008
JP    2010-136831 A    6/2010
(Continued)

OTHER PUBLICATIONS

Korean Intellectual Property Office, International Search Report for International Application No. PCT/KR2013/002472, dated Jul. 2, 2013.

*Primary Examiner* — Gary Jackson
*Assistant Examiner* — Zahed Kabir
(74) *Attorney, Agent, or Firm* — Dinsmore & Shohl LLP; Yongsok Choi, Esq.

(57) ABSTRACT

The present invention relates to a minimally invasive surgical instrument having an articulation immobilizing structure. The present invention is a minimally invasive surgical instrument and includes a shaft, an end effector connected towards one end of the shaft, a wire for controlling the articulated movement of the end effector, and an immobilizing structure adapted to immobilize the state of articulated movement of the end effector. The immobilizing structure includes a resilient member covering the wire, and the resilient member holds the wire when an internal space therein contracts.

4 Claims, 8 Drawing Sheets

(52) U.S. Cl.
CPC ............... *A61B 2017/2927* (2013.01); *A61B 2017/2946* (2013.01)

(58) Field of Classification Search
USPC ..................................... 606/1, 206
See application file for complete search history.

(56) References Cited

U.S. PATENT DOCUMENTS

| | | | |
|---|---|---|---|
| 2009/0108048 A1* | 4/2009 | Zemlok | A61B 17/07207 227/175.1 |
| 2010/0191278 A1* | 7/2010 | Lee | A61B 17/062 606/206 |
| 2012/0059408 A1* | 3/2012 | Mueller | A61B 17/29 606/206 |

FOREIGN PATENT DOCUMENTS

| | | |
|---|---|---|
| JP | 2010-207340 A | 9/2010 |
| KR | 10-1075294 B1 | 10/2011 |

* cited by examiner

MINIMALLY INVASIVE SURGICAL INSTRUMENT HAVING ARTICULATION IMMOBILISING STRUCTURE

FIELD OF THE INVENTION

The present invention relates to a minimally invasive surgical instrument having a joint fixing structure.

BACKGROUND

Minimally invasive surgery is a surgical approach that involves the use of instruments inserted through at least one tiny incision opening to perform a surgery causing minimal tissue trauma in human or animal bodies.

The minimally invasive surgery relatively reduces changes in metabolism of a patient in the period of post-surgical care, so it facilitates rapid recovery of the patient. Therefore, the minimally invasive surgery shortens the length of hospitalization of the patient after the surgery and allows the patient to return to normal physical activities in a short period of time. In addition, the minimally invasive surgery causes less pain and leaves fewer scars on the patient's body after the surgery.

One of the general forms of the minimally invasive surgery is endoscopy. Among the others, a laparoscopy that involves minimally invasive inspection and operation inside abdominal cavity is known as the most general form of endoscopy. To operate a standard laparoscopic surgery, the abdomen of the patient is insufflated with gas and at least one small incision is formed to provide an entrance for laparoscopic surgical instruments, through which a trocar is inserted. When performing the surgery, it is general that a user puts the laparoscopic surgical instruments into a surgical site or the like through the trocar, and manipulates (or controls) the instruments from the outside of abdominal cavity. In general, the laparoscopic surgical instruments include a laparoscope (for observation of a surgical site) and other working tools. Herein, the working tools are similar to the conventional tools used for small incision surgery, except that the end effector or working end of each tool is separated from its handle or the like by a shaft. For instance, the working tools may include a clamp, a grasper, scissors, a stapler, a needle holder, and so forth. Meanwhile, the user monitors the procedure of the surgery through a monitor that displays the images of the surgical site which are taken by the laparoscope. The endoscopic approaches similar to the above are broadly used in retroperitoneoscopy, pelviscopy, arthroscopy, cisternoscopy, sinuscopy, hysteroscopy, nephroscopy, cystoscopy, urethroscopy, pyeloscopy, and so on.

The inventor(s) has developed various minimally invasive surgical instruments useful for the above-mentioned minimally invasive surgeries and has already disclosed the features of the structures and effects of the same in Korean Patent Application Nos. 2008-51248, 2008-61894, 2008-79126 and 2008-90560, the contents of which are to be regarded as being incorporated herein by reference in its entirety. Additionally, the inventor(s) have also introduced a minimally invasive surgical instrument with improved functionality, which is more advantageous for users and patients, in Korean Patent Application Nos. 2010-115152, 2011-3192, 2011-26243, 2011-29771, 2011-86738, 2011-89854 and the like, the contents of which are to be regarded as being incorporated herein by reference in its entirety.

Herein, the inventor(s) now present a joint fixing structure having excellent capabilities, which may be widely employed in the minimally invasive surgical instruments disclosed in the aforementioned Korean patent applications or other minimally invasive surgical instruments.

SUMMARY OF THE INVENTION

One object of the present invention is to provide a minimally invasive surgical instrument having a joint fixing structure to hold a wire for controlling joint motion of an end effector so that the state of the joint motion thereof may be firmly fixed.

According to one aspect of the invention to achieve the object as described above, there is provided a minimally invasive surgical instrument comprising a shaft; an end effector being connected to one end of the shaft; a wire to control joint motion of the end effector; and a fixing structure to fix the state of the joint motion of the end effector, wherein the fixing structure comprises an elastic member surrounding the wire, and the elastic member holds the wire as an internal space thereof is reduced.

According to the invention, there is provided a minimally invasive surgical instrument having a joint fixing structure to hold a wire for controlling joint motion of an end effector so that the state of the joint motion thereof may be firmly fixed.

DETAILED DESCRIPTION OF THE PREFERRED EMBODIMENTS

Figure 1:
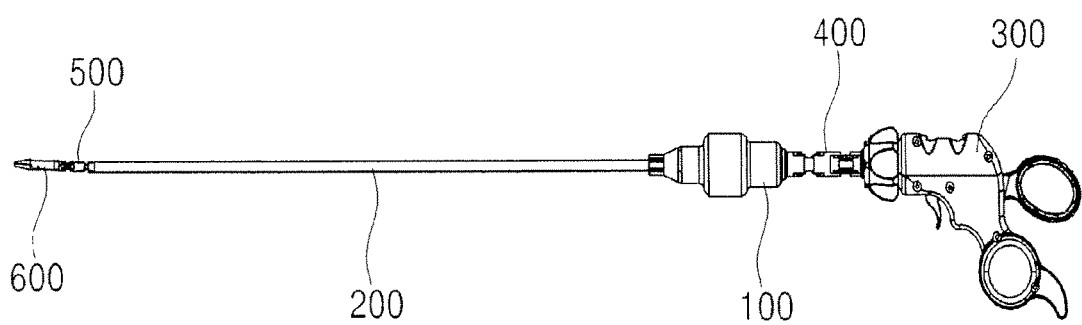
FIG. 1 shows the overall appearance of a minimally invasive surgical instrument according to one embodiment of the invention.

In the following detailed description of the present invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures and characteristics described herein may be implemented as modified from one embodiment to another without departing from the spirit and scope of the invention. Furthermore, it shall be understood that the locations or arrangements of individual components within each embodiment may also be modified without departing from the spirit and scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, preferred embodiments of the present invention will be described in detail with reference to the accompanying drawings to enable those skilled in the art to easily implement the invention.

Meanwhile, it should be understood that the term "connection" herein encompasses a direct connection or an indirect connection (i.e., via separate components) between mechanical or other types of components. For example, a connection between two rotating components may be a direct connection formed by the engagement of corresponding gear elements or the like, but may also be an indirect connection via a separate component such as a cable or a groove.

FIG. 1 shows the overall appearance of a minimally invasive surgical instrument according to one embodiment of the invention.

Reference will be made to FIG. 1. The minimally invasive surgical instrument may comprise a fixing structure (i.e. joint fixing structure) 100; a shaft 200 being connected to the fixing structure 100; a handling unit 300 that may be manipulated by a user; a first joint unit 400 being connected and disposed between the fixing structure 100 and the handling unit 300 to cause joint motion or the like of an end effector 600 (to be described below) according to the user's manipulation of the handling unit 300; a second joint unit 500 to allow the end effector 600 to carry out joint motion or the like in cooperation with the first joint unit 400; and the end effector 600 being connected to one end of the shaft 200 via the second joint unit 500 to perform surgery by using surgical tools (not shown) or functioning itself as a surgical tool.

First, the shaft 200 may include a cavity therein to support and pass at least one wire (not shown) or torque transmission member (not shown), in the same manner as those of the minimally invasive surgical instruments disclosed in the aforementioned Korean patent applications of the applicant (s). (The torque transmission member is mainly intended for rolling motion of the end effector 600, while the shaft 200 may function itself as the torque transmission member in some cases.) The shaft 200 may comprise at least one segment as necessary. Further, the shaft 200 may comprise a bend in at least a part thereof.

Next, the handling unit 300 may control joint motion, rolling motion, opening/closing motion and the like of the end effector 600 according to the user's manipulation, in the same manner as those of the minimally invasive surgical instruments disclosed in the aforementioned Korean patent applications of the applicant(s). To allow for such control, the at least one wire or torque transmission member may be connected to the handling unit 300.

Next, the first and second joint units 400 and 500 may act together with the at least one wire or torque transmission member to allow the end effector 600 to carry out joint motion, rolling motion and the like, in the same manner as those of the minimally invasive surgical instruments disclosed in the aforementioned Korean patent applications of the applicant(s).

Next, the end effector 600 may carry out joint motion, rolling motion, opening/closing motion and the like by the action of the at least one wire or torque transmission member passing from the handling unit 300 to the second joint unit 500 via the first joint unit 400 and the shaft 200, in the same manner as those of the minimally invasive surgical instruments disclosed in the aforementioned Korean patent applications of the applicant(s). The tip of the end effector 600 may be implemented in the form of a clamp, a grasper, a pair of scissors, a stapler, a needle holder, a hook-type electrode or the like.

Finally, the fixing structure 100 may hold a wire for controlling joint motion or the like of the end effector 600 so that the state of the joint motion of the end effector 600 may be firmly fixed.

Figure 2:
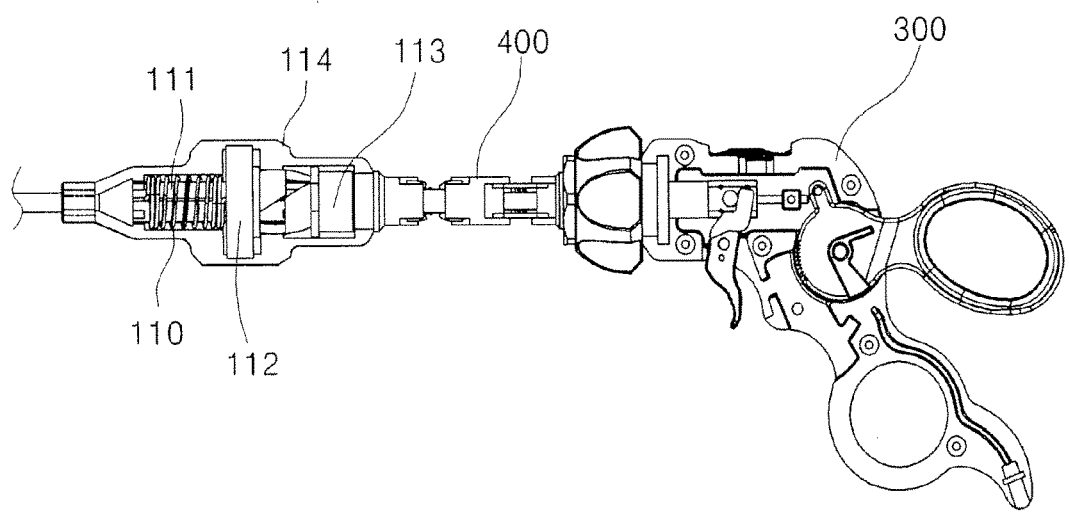
FIG. 2 is a partial cross-sectional view of the minimally invasive surgical instrument shown in FIG. 1.

FIG. 2 is a partial cross-sectional view of the minimally invasive surgical instrument shown in FIG. 1. The fixing structure 100 will be discussed below with further reference to FIG. 2.

The fixing structure 100 may comprise a spring 110 (preferably in the form of a coil). Further, the fixing structure 100 may comprise a wire guide path (e.g. a groove or pipe) extending from the handling unit 300 via the first joint unit 400, or may further comprise a wire fixing assistance member 111 that may support the wire and assist it to be fixed. (In connection with one exemplary shape of the wire fixing assistance member 111, reference may be made to FIG. 3.) The spring 110 may surround the outer surface of the wire fixing assistance member 111.

One end of the spring 110 may be connected to a rotational motion member 112. Further, the other end of the spring 110 may be fixed to a case 114 or the like to be described below. Accordingly, a part of the spring 110 is rotated when the rotational motion member 112 carries out rotational motion, so that the spring 100 may be twisted on the whole. The rotational motion member 112 may contact a linear motion member 113. The above components may be disposed within the case 114, which surrounds and covers them.

Figure 3:
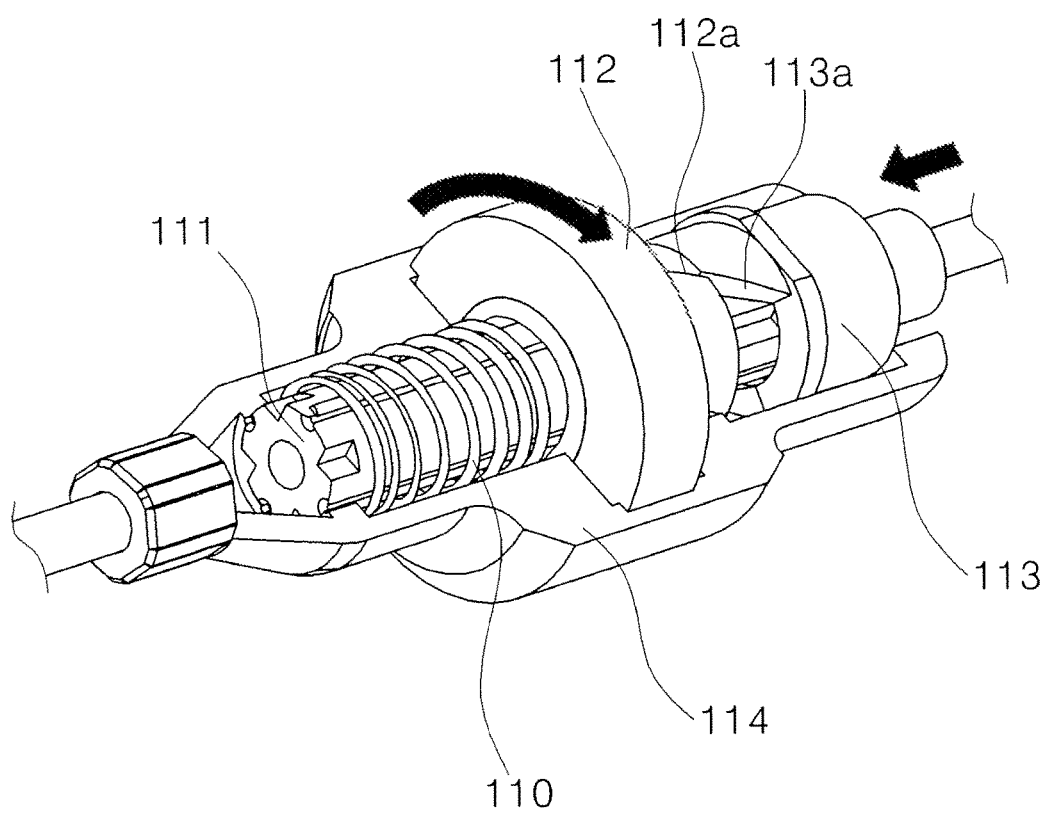
FIG. 3 is a partial cross-sectional view of a fixing structure 100 shown in FIG. 2.

FIG. 3 is a partial cross-sectional view of the fixing structure 100 shown in FIG. 2. Further reference will be made to FIG. 3.

The rotational motion member 112 may comprise a slope 112a at the portion contacting the linear motion member 113, and the linear motion member 113 may also comprise a slope 113a at the corresponding portion. Thus, when the slope 113a applies a force to the slope 112a by the action of the linear motion member 113 (e.g., the action in which the linear motion member 113 carries out linear motion toward the rotational motion member 112 according to the manipulation of the handling unit 300 and then the state of the motion thereof is fixed), the rotational motion member 112 may rotate so that the spring 110 may be rotated and twisted. The slope directions of the two slopes 112a and 113a may be determined such that the spring 110 is rotated and twisted according to the rotation of the rotational motion member 112. In case of FIG. 3, the slope directions of the slopes 112a and 113a are determined as illustrated because the spring 110 is rotated and twisted when the rotational motion member 112 rotates counterclockwise (as seen from the linear motion member 113).

When the spring 110 is rotated and twisted by the action of the linear motion member 113 and the rotational motion member 112, an internal space of the portion where the spring 110 surrounds the outer surface of the wire fixing assistance member 111 may be reduced. The spring 110 may accordingly tighten the wire fixing assistance member 111 and further the wire guided or supported by the wire fixing assistance member 111, so that the wire may be fixed.

Figure 4:
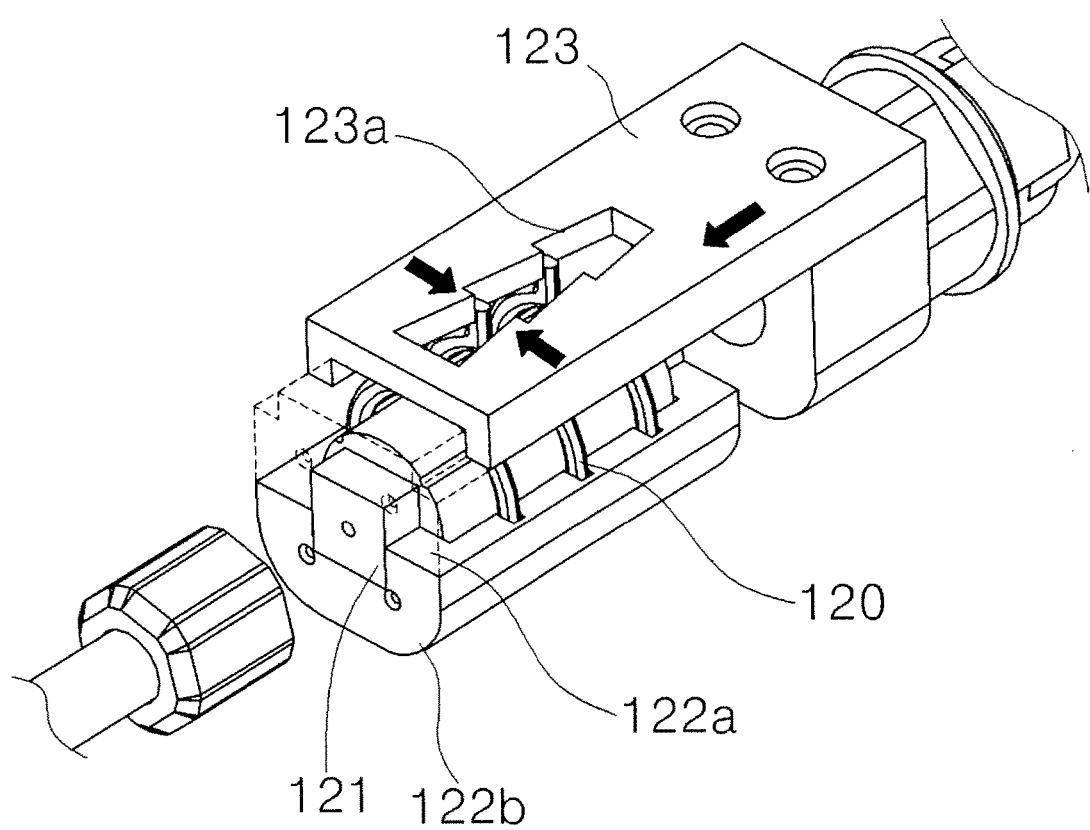
FIG. 4 is a perspective view of a fixing structure 100 according to another embodiment of the invention.
Figure 5:
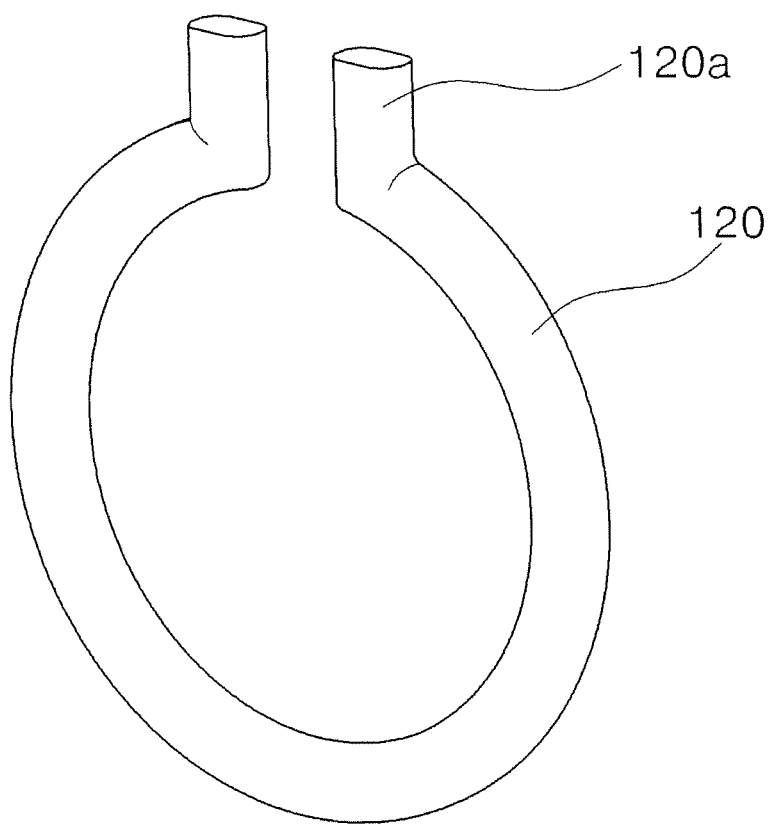
FIG. 5 shows a C-shaped ring 120 among the components of the fixing structure 100 shown in FIG. 4.

FIG. 4 is a perspective view of a fixing structure 100 according to another embodiment of the invention. Further, FIG. 5 shows a C-shaped ring 120 among the components of the fixing structure 100 shown in FIG. 4. According to the present embodiment, the C-shaped ring 120 is employed instead of the spring 110 so that an internal space of the portion where it surrounds a wire fixing assistance member 121 may be reduced, thereby fixing the wire.

The C-shaped ring 120 according to the present embodiment (preferably a plurality of the C-shaped rings 120) may surround the wire fixing assistance member 121. The C-shaped ring 120 may comprise protrusions 120a at both ends thereof, and the protrusions 120a may be disposed in a groove 123a formed in a linear motion member 123. As illustrated, the groove 123a may be formed (preferably in the form of a wedge or similar shape) such that an interval between the protrusions 120a is reduced by the action of the linear motion member 123 (e.g., when the linear motion member 123 carries out linear motion toward the shaft 200) to allow the C-shaped ring 120 to tighten the wire fixing assistance member 121. Therefore, the present embodiment may also fix the wire as in the above-described embodiment. Meanwhile, the portions of the C-shaped ring 120 and the wire fixing member 121 except the protrusions 120a may be covered by covers 122a and 122b, and one end of the wire fixing assistance member 121 (represented as a cuboid-like shape in FIG. 4) may allow the wire fixing assistance member 121 to be fixed to the covers 122a and 122b to a certain degree.

Figure 6:
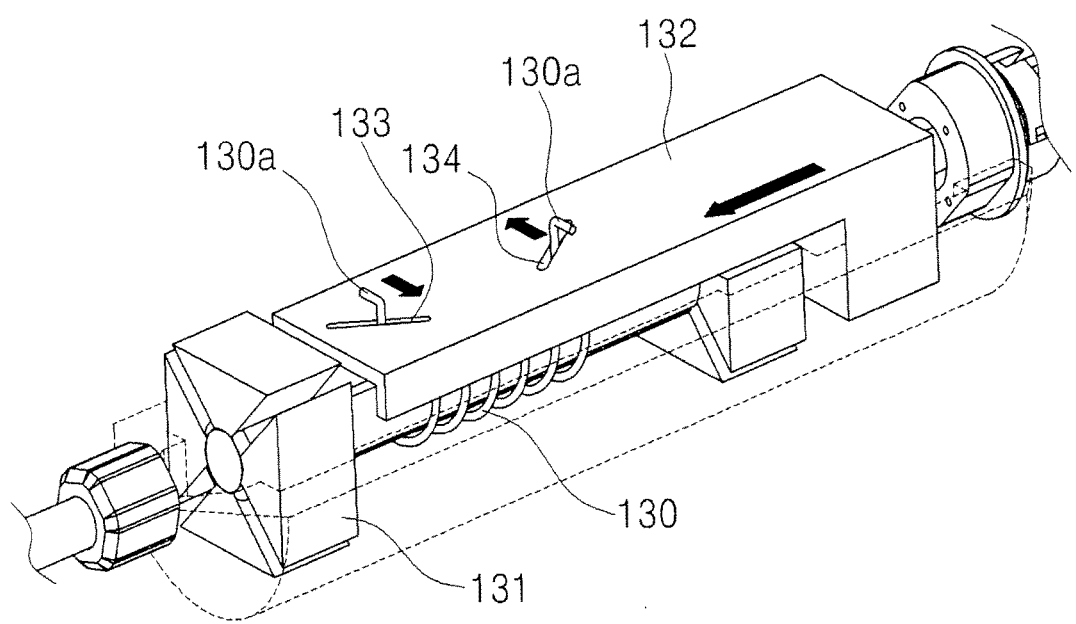
FIG. 6 is a perspective view of a fixing structure 100 according to yet another embodiment of the invention.

FIG. 6 is a perspective view of a fixing structure 100 according to yet another embodiment of the invention. According to the present embodiment, a spring 130 is employed wherein a linear motion member 132 acts on both ends thereof so that an internal space of the portion where the spring 130 surrounds the outer surface of a wire fixing assistance member 131 may be reduced, thereby fixing the wire.

The spring 130 according to the present embodiment may surround the outer surface of the wire fixing assistance member 131. Protrusions 130a may be formed at both ends of the spring 130. Meanwhile, the linear motion member 132 may comprise a front groove 133 and a rear groove 134 to allow the linear motion member 132 to act on the protrusions 130a of the spring 130 when it carries out linear motion toward the shaft 120, so that the spring 130 may tighten the wire fixing assistance member 131. (The protrusions 130a may be inserted in the front and rear grooves 133 and 134.) As illustrated, the front and rear grooves 133 and 134 may be formed to be inclined with respect to the direction in which the linear motion member 132 carries out linear motion toward the shaft 200, and to have the opposite inclinations. Therefore, the present embodiment may also fix the wire as in the above-described embodiments.

Figure 7:
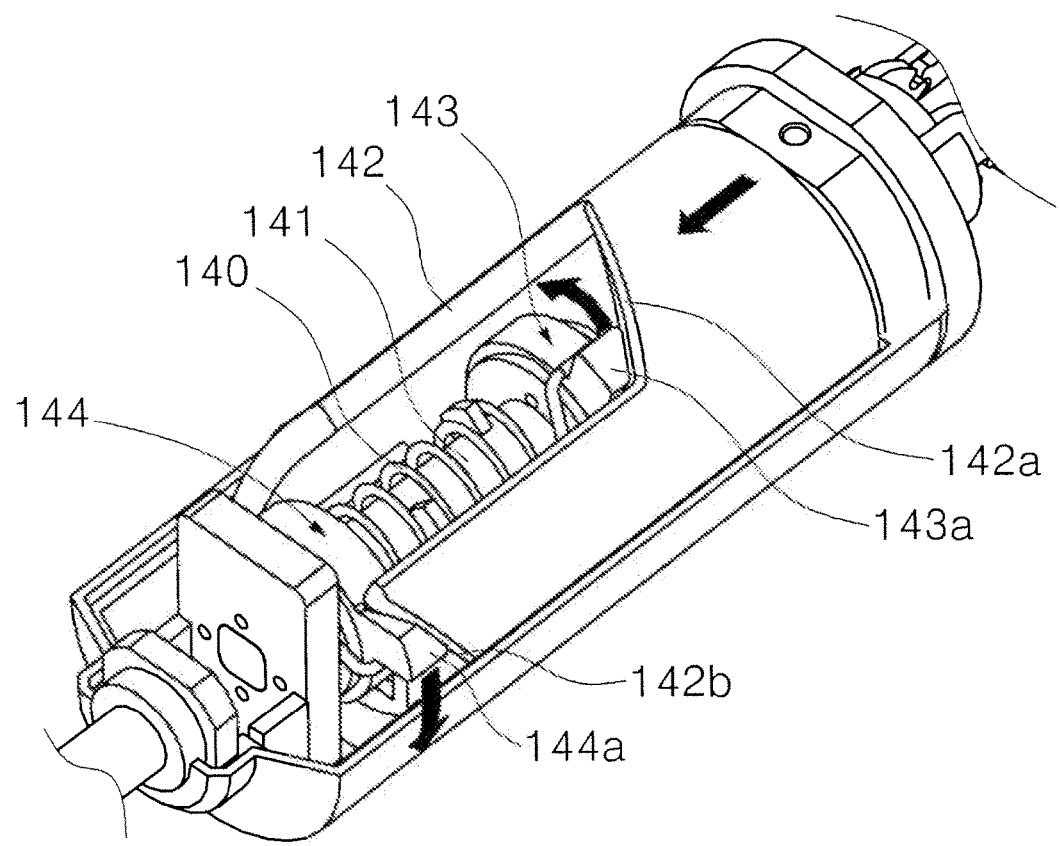
FIG. 7 is a perspective view of a fixing structure 100 according to still another embodiment of the invention.
Figure 8:
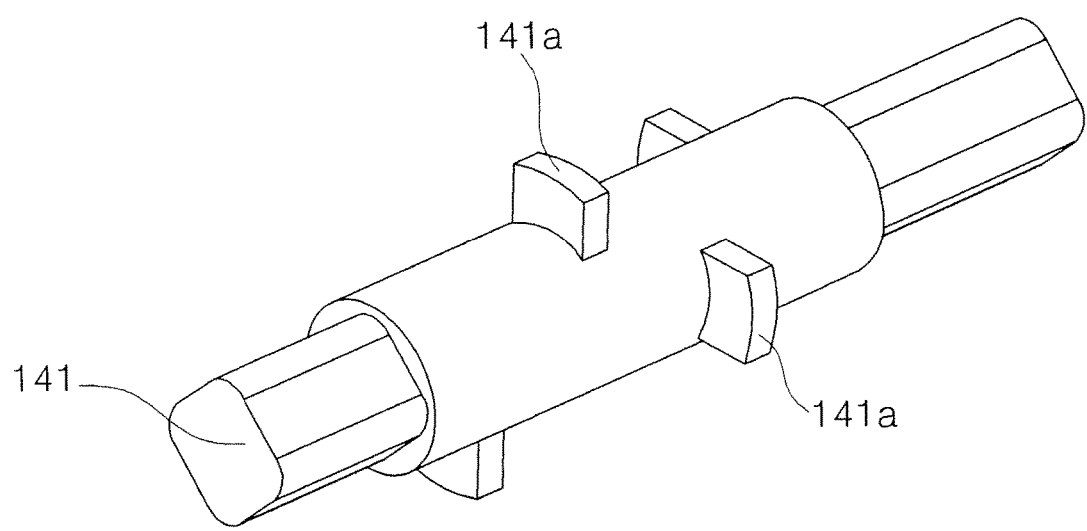
FIG. 8 is a perspective view of a wire fixing assistance member 141 among the components of the fixing structure 100 shown in FIG. 7.

FIG. 7 is a perspective view of a fixing structure 100 according to still another embodiment of the invention. Further, FIG. 8 is a perspective view of a wire fixing assistance member 141 among the components of the fixing structure 100 shown in FIG. 7. According to the present embodiment, a spring 140 is employed wherein the spring 140 is twisted by means of two rotational motion members 143 and 144, which are connected to both ends of the spring 140, by the action of a linear motion member 142 so that an internal space of the portion where the spring 140 surrounds the outer surface of the wire fixing assistance member 141 may be reduced, thereby fixing the wire.

The spring 140 according to the present embodiment may surround the outer surface of the wire fixing assistance member 141. Both ends of the spring 140 may be connected to the first and second rotational motion members 143 and 144, respectively. Therefore, when the first and second rotational motion members 143 and 144 rotate in the opposite directions, the spring 140 may accordingly be twisted. Meanwhile, the first and second rotational motion members 143 and 144 may comprise protrusions 143a and 144a, respectively.

Further, the linear motion member 142 may be further provided. The linear motion member 142 may comprise a first slope 142a and a second slope 142b. The first and second slopes 142a and 142b may be respectively inclined in a direction to enable the first and second rotational motion members 143 and 144 to carry out the rotational motion as above. (Correspondingly, the protrusions 143a and 144a may also comprise slopes.)

Accordingly, when the linear motion member 142 carries out linear motion toward the shaft 200, for example, the first slope 142a applies a force to the protrusion 143a to allow the first rotational motion member 143 to rotate clockwise (as seen from the handling unit 300), and the second slope 142b applies a force to the protrusion 144a to allow the second rotational motion member 144 to rotate counterclockwise. Therefore, the present embodiment may also fix the wire as in the above-described embodiments. Meanwhile, as illustrated in FIG. 8, the wire fixing assistance member 141 may comprise a spring fixing unit 141a, which may prevent the spring 140 from unnecessarily moving toward the shaft 200 or in the opposite direction or the like. A component such as the spring fixing unit 141a may also be used in the above other embodiments employing a spring.

Applications

According to an application of the present invention, those skilled in the art may partially change the form and such of the handling unit or the like so that the wire or torque transmission member of the minimally invasive surgical instrument may be operated or fixed by an electric motor or the like of another motor-based system (not shown) such as a surgical robot, as necessary.

Although the present invention has been described in terms of specific items such as detailed components as well as the limited embodiments and the drawings, they are only provided to help general understanding of the invention, and the present invention is not limited to the above embodiments. It will be appreciated by those skilled in the art that various modifications and changes may be made from the above description.

Therefore, the spirit of the present invention shall not be limited to the above-described embodiments, and the entire scope of the appended claims and their equivalents will fall within the scope and spirit of the invention.

What is claimed is:

1. A minimally invasive surgical instrument, comprising:
a shaft;
an end effector being connected to one end of the shaft;
a wire to control articulating motion of the end effector; and
a fixing structure to fix a state of the articulating motion of the end effector,
wherein the fixing structure comprises an elastic member;
the fixing structure further comprises a wire fixing assistance member to guide or support the wire;
the fixing structure further comprises a rotational motion member, the rotational motion member being rotatable along an axis of the shaft;
the elastic member is a spring one end of which is connected to the rotational motion member;
the spring surrounds the wire and the wire fixing assistance member; and an internal space of the spring is reduced as the rotational motion member rotates.

2. The minimally invasive surgical instrument as claimed in claim 1, wherein the wire fixing assistance member comprises a wire guide path.

3. The minimally invasive surgical instrument as claimed in claim 1, wherein the fixing structure further comprises a linear motion member, and the internal space of the elastic member is reduced as the linear motion member carries out linear motion.

4. The minimally invasive surgical instrument as claimed in claim 1, wherein the wire fixing assistance member comprises a fixing unit to restrict the movement of the elastic member.

* * * * *